United States Patent
Warren

(10) Patent No.: US 8,413,656 B2
(45) Date of Patent: Apr. 9, 2013

(54) MEDICAL SYSTEM

(76) Inventor: Julio A. Warren, Petersburg, FL (US)

( * ) Notice: Subject to any disclaimer, the term of this patent is extended or adjusted under 35 U.S.C. 154(b) by 222 days.

(21) Appl. No.: 13/066,069

(22) Filed: Apr. 6, 2011

(65) Prior Publication Data

US 2012/0255554 A1  Oct. 11, 2012

(51) Int. Cl.
*A61M 16/04* (2006.01)
(52) U.S. Cl. .............................. 128/206.25; 128/858
(58) Field of Classification Search .................. None
See application file for complete search history.

(56) References Cited

U.S. PATENT DOCUMENTS

| | | | | |
|---|---|---|---|---|
| 2,572,638 A | * | 10/1951 | Loos | 128/858 |
| 4,867,146 A | * | 9/1989 | Krupnick et al. | 128/858 |
| 5,593,759 A | * | 1/1997 | Vargas et al. | 428/200 |
| 5,647,357 A | * | 7/1997 | Barnett et al. | 128/206.21 |
| 5,887,590 A | * | 3/1999 | Price | 128/858 |
| 6,651,661 B2 | * | 11/2003 | Matioc | 128/206.21 |
| 6,764,459 B1 | * | 7/2004 | Donaldson | 602/74 |
| 6,982,107 B1 | * | 1/2006 | Hennen | 428/40.1 |
| 2002/0134388 A1 | * | 9/2002 | Chang | 128/206.21 |

* cited by examiner

*Primary Examiner* — Loan Thanh
*Assistant Examiner* — Andrew S Lo

(57) ABSTRACT

A respiratory anesthesia mask has an exposed face. The mask has an interior periphery in a continuous loop to fit a face of a patient. The mask having a centrally located exterior cylinder adapted to couple with a source of respiratory anesthesia gas. The mask has an intermediate section in a generally frusto-conical configuration between the interior periphery and the tube. Eyelid closure and protection equipment is received and supported on the face of the intermediate section of the mask. The closure and protection equipment includes two repositionable adhesive strips with interior and exterior surfaces. The closure and protection equipment includes temporary adhesive on the interior surface of the repositionable adhesive strip. In this manner, the repositionable adhesive strips are removably coupled to the face of the intermediate section of the mask.

11 Claims, 4 Drawing Sheets

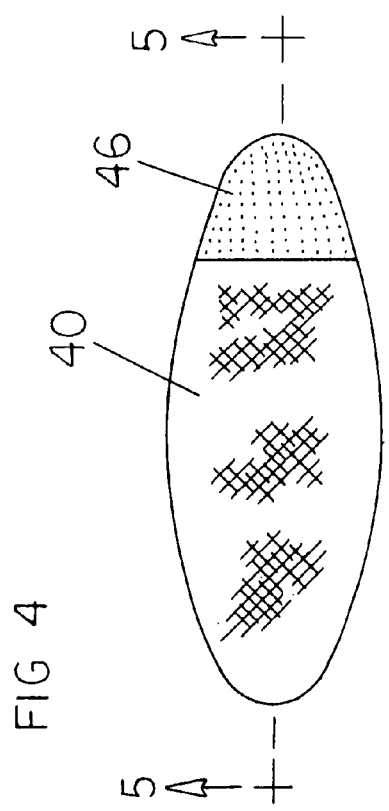
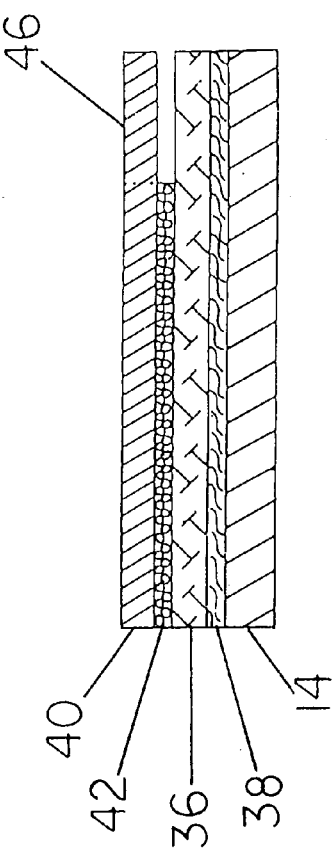
FIG 4
FIG 5

MEDICAL SYSTEM

BACKGROUND OF THE INVENTION

1. Field of the Invention

The present invention relates to a medical system and more particularly pertains to protecting vulnerable eyes of a patient during general anesthesia, the protection being done in a safe, sanitary, reliable, convenient, timely and economical manner.

Twenty million patients in the United States undergo general anesthesia each year. In 1992, an American Society of Anesthesiologists Closed Claims Project reported that eye injuries account for 3 percent of all anesthesia-related malpractice claims; 35 percent of these were related to injuries of the cornea.

Twenty percent of corneal abrasions occur when direct trauma or chemical irritants injure the eye. In addition, general anesthesia reduces tear production and stability, thereby exposing patients' eyes to increased risk of drying and abrasion of the cornea. This injurious exposure-induced drying of the cornea occurs in 44 percent of patients with partially open eyelids during anesthesia.

Distracting events during the induction phase of general anesthesia are frequent and have been shown in a European study to have a negative impact on patient management in one in five cases. Eye protection is generally recommended immediately after this phase, once the patient is anesthetized. Distractions during this critical period may delay deployment of eye protection maneuvers. In fact, failure to protect the eyes in a timely fashion, if at all, has been implicated in corneal abrasions by identifying novice anesthesia providers as independent risk factors for this type of injury. Typically, the anesthesiologist tapes the eyes fully shut with a medical tape, often requiring him to turn his attention away from the patient while reaching for tape elsewhere on the anesthesia workstation.

2. Description of the Prior Art

The use of masks of known designs and configurations is known in the prior art. More specifically, masks of known designs and configurations consist basically of familiar, expected, and obvious structural configurations, notwithstanding the myriad of designs encompassed by the crowded prior art which has been developed for the fulfillment of countless objectives and requirements.

By way of example, U.S. Pat. No. 3,949,742 issued Apr. 13, 1975 to Nowakowsi relates to a Medical Dressing. U.S. Pat. No. 4,062,361 issued Dec. 13, 1975 to Poulsen relates to a Bilaminar Ostomy Sealing Disk. U.S. Pat. No. 4,302,500 issued Nov. 24, 1981 to Flora relates to a Breathable Surgical Adhesive Tape. U.S. Pat. No. Des. 397,215 issued Aug. 18, 1998 to Hoftman relates to a Face Mask without an Inflatable Cuff. U.S. Pat. No. 5,887,590 issued Mar. 30, 1999 to Price relates to an Eyelid Closure Patch. U.S. Pat. No. 6,035,852 issued Mar. 14, 2000 to Hoftman relates to an Inflated Cuff Anesthesia/Respiratory Mask with Improved Nasal/Maxilla Bone Adaption. Lastly, U.S. Patent Application Publication Pub. No.: US 2007/0295335 to Nashed published Dec. 27, 2007 relates to a Disposable Anesthesia Face Mask.

While these devices fulfill their respective, particular objectives and requirements, the aforementioned patents do not describe an integrated medical system that allows for protecting vulnerable eyes of a patient during general anesthesia, the protection being done in a safe, sanitary, reliable, convenient, timely and economical manner.

In this respect, the medical system according to the present invention substantially departs from the conventional concepts and designs of the prior art, and in doing so provides an apparatus primarily developed for the purpose of protecting vulnerable eyes of a patient during general anesthesia, the protection being done in a safe, sanitary, reliable, convenient, timely and economical manner.

Therefore, it can be appreciated that there exists a continuing need for a new and improved medical system which can be used for protecting vulnerable eyes of a patient during general anesthesia, the protection being done in a safe, sanitary, reliable, convenient, timely and economical manner. In this regard, the present invention substantially fulfills this need.

SUMMARY OF THE INVENTION

In view of the foregoing disadvantages inherent in the known types of masks of known designs and configurations now present in the prior art, the present invention provides an improved medical system. As such, the general purpose of the present invention, which will be described subsequently in greater detail, is to provide a new and improved medical system and method which has all the advantages of the prior art and none of the disadvantages.

To attain this, the present invention essentially comprises a medical system. First provided is a respiratory anesthesia mask. The mask is adapted to receive and removably support eyelid closure and protection equipment. In this manner, patient eye safety is prioritized. The mask has an exposed face. The mask has an interior periphery. The interior periphery is provided in a continuous loop. The interior periphery is ergonomically designed to fit the contours of a face of a patient. The interior periphery is designed in a comfortable manner for the patient. The interior periphery is further designed to avoid physical contact with the eyes of the patient. The mask has a caudad portion. The caudad portion has a broad width. The mask has a cephalad portion. The cephalad portion has a narrow width less than the broad portion. The mask has an air-filled tubular bladder. The bladder is provided in a continuous loop. The bladder is provided overlying the interior periphery. In this manner, patient comfort is enhanced through a cushioned mask fit while a low pressure seal is provided between the mask and a face of the user. A valve is coupled to the bladder for increasing and decreasing the pressure within the bladder The mask has a centrally located exterior cylinder. The exterior cylinder is adapted to couple with a source of respiratory anesthesia gas for delivery to a patient. The cylinder has a ring with hooks to facilitate coupling the mask to a patient via a strap or other fastening device.

The mask has an intermediate section. The intermediate section is in a generally frusto-conical configuration. The intermediate section is provided between the interior periphery and the tube.

The mask is fabricated of a hypo-allergenic plastic. In this manner, the comfort and safety of the patient are enhanced. The mask is adapted to be fabricated of non-latex, sterile or non-sterile materials. The plastic of the mask is clear and transparent, preferably a thermoset hard plastic. In this manner, uninterrupted surveillance of the patient and readily exhibited condensation characteristic of expiration of gas from the patient are provided. The mask is intended for single patient use. In this manner, costly sterilization and reprocessing expenses are eliminated. Also in this manner, contamination of medical equipment from one patient to another is prevented.

Eyelid closure and protection equipment is provided. The closure and protection equipment is received and supported on the face of the intermediate section of the mask on opposite sides of the cylinder. The closure and protection equipment includes two oval-shaped fixed release strips. The fixed release strips have interior and exterior surfaces. A permanent adhesive is provided. The permanent adhesive is provided on the entire interior surface of the fixed release strip. In this manner, the fixed release strips are permanently coupled to the face of the intermediate section of the mask. The closure and protection equipment includes two oval shaped repositionable adhesive strips. The repositionable adhesive strips have interior and exterior surfaces. A temporary adhesive is provided. The temporary adhesive is provided on between 60 and 90 percent of interior surface of the repositionable adhesive strips. In this manner, the repositionable adhesive strips are adjustably coupled to the exterior surfaces of the fixed release strips. The fixed release strips and the repositionable adhesive strips are each provided in an oval configuration. The fixed release strips and the repositionable adhesive strips each have a major axis between 1.5 and 2.5 inches and a minor axis between 1 and 1.5 inches. The portions of the repositionable adhesive strips without adhesive are provided closer to the caudad portion of the mask than to the cephalad portion of the mask.

The eyelid closure and protection equipment is integrated into the respiratory anesthesia mask, one at each side with repositionable adhesive strips. The dimensions of the repositionable adhesive strips exceed the size of a human eye. In this manner, complete coverage is allowed. The adhesive properties are only adapted to apply to the side of the repositionable adhesive strips in contact with the fixed release strips. Once removed during use, the repositionable adhesive strips remain in contact with the patient. The repositionable adhesive strips are intended for single patient use. In this manner, costly sterilization and reprocessing expenses are eliminated. Also in this manner, contamination of medical equipment from one patient to another is prevented. The repositionable adhesive strips are non-latex. In this manner, the risk of latex exposure, latex allergy, and latex sensitization for patient and healthcare provider is prevented. The repositionable adhesive strips have hypoallergenic properties. In this manner, irritation of the eyes, eyelids, and surrounding skin is reduced. The strips are waterproof. In this manner, the equipment is protected from loss of integrity and adhesion and able to maintain eyelid closure and protection. The strips are transparent. In this manner, uninterrupted surveillance of the patient is allowed.

Tabs are provided. The tabs are formed as parts of the repositionable adhesive strips. The tabs are formed without adhesive there beneath. In this manner, the adhesive strips will remain attached to the mask until the healthcare provider efficiently lifts the tabs and raises the entire repositionable adhesive strip efficiently just prior to application to the patient. The tab is a raised edge of one of the repositionable adhesive strips with no adhesive but contiguous with the remainder of the repositionable adhesive strip which has adhesive on its undersurface. The tab is adapted to be grasped and pulled by the health care provider. In this manner, careful removal of the strip from the patient at the conclusion of use, whether for both procedure and general anesthetic, is facilitated. Further in this manner, trauma to and bruising of the eyelid is prevented. The repositionable adhesive strips are located on the mask. The repositionable strips are always visible to the healthcare provider as he monitors the patient. The presence and position of the repositionable strips thereby serve as a constant reminder to employ the eye protection measure as soon as loss of consciousness is achieved and lessen the chance of distractions and interruptions, normally common during clinical activities of this busy period, which can impact timely performance and increase the risk of errors of omission and patient injury.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved medical system which has all of the advantages of the prior art masks of known designs and configurations and none of the disadvantages.

It is another object of the present invention to provide a new and improved medical system which may be easily and efficiently manufactured and marketed.

It is further object of the present invention to provide a new and improved medical system which is of durable and reliable constructions.

An even further object of the present invention is to provide a new and improved medical system which is susceptible of a low cost of manufacture with regard to both materials and labor, and which accordingly is then susceptible of low prices of sale, thereby making such medical system economically available to patients.

Even still another object of the present invention is to provide a medical system for protecting vulnerable eyes of a patient during general anesthesia, the protection being done in a safe, sanitary, reliable, convenient, timely and economical manner.

Lastly, it is an object of the present invention to provide a new and improved medical system. A respiratory anesthesia mask has an exposed face. The mask has an interior periphery in a continuous loop to fit a face of a patient. The mask has a centrally located exterior cylinder adapted to couple with a source of respiratory anesthesia gas. The mask has an intermediate section in a generally frusto-conical configuration between the interior periphery and the tube. Eyelid closure and protection equipment is received and supported on the face of the intermediate section of the mask. The closure and protection equipment includes two repositionable adhesive strips with interior and exterior surfaces. The closure and protection equipment includes temporary adhesive on the interior surface of the repositionable adhesive strip. In this manner, the repositionable adhesive strips are removably coupled to the face of the intermediate section of the mask.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is a plan view of the eye closure and protection equipment of the respiratory anesthesia mask system shown in FIGS. 1-3.

FIG. 5 is a cross sectional view of the eye closure and protection equipment taken along line 5-5 of FIG. 4.

The same reference numerals refer to the same parts throughout the various Figures.

DESCRIPTION OF THE PREFERRED EMBODIMENT

Figure 1:
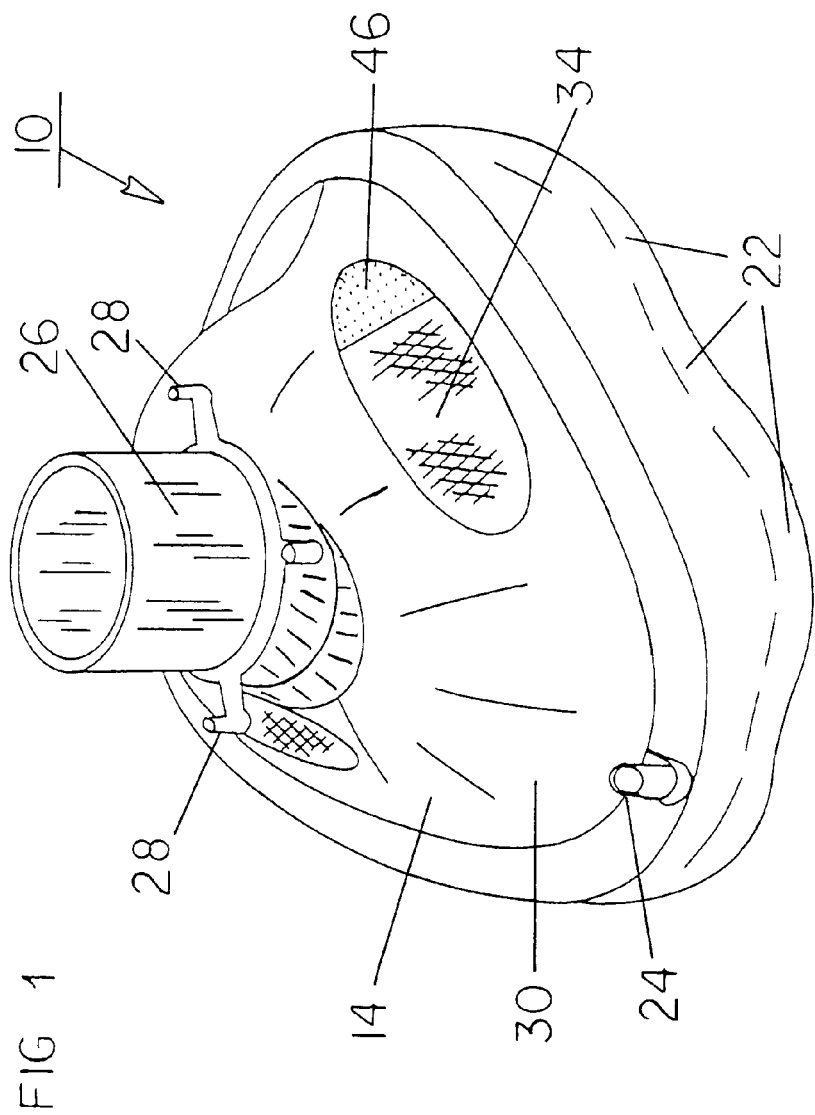
FIG. 1 is a perspective illustration of a respiratory anesthesia mask constructed in accordance with the principles of the present invention.
Figure 2:
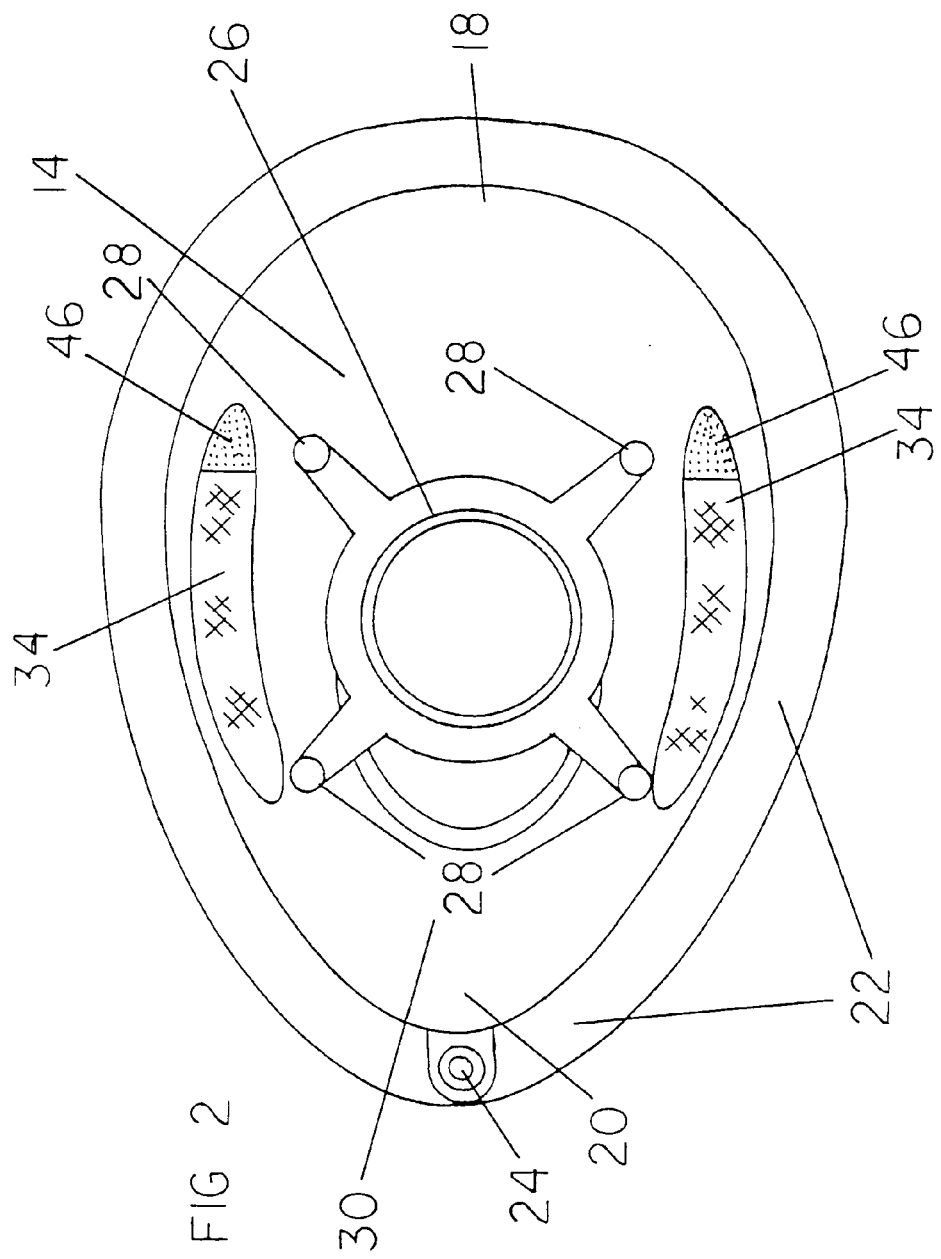
FIG. 2 is a plan view of the respiratory anesthesia mask system shown in FIG. 1.
Figure 3:
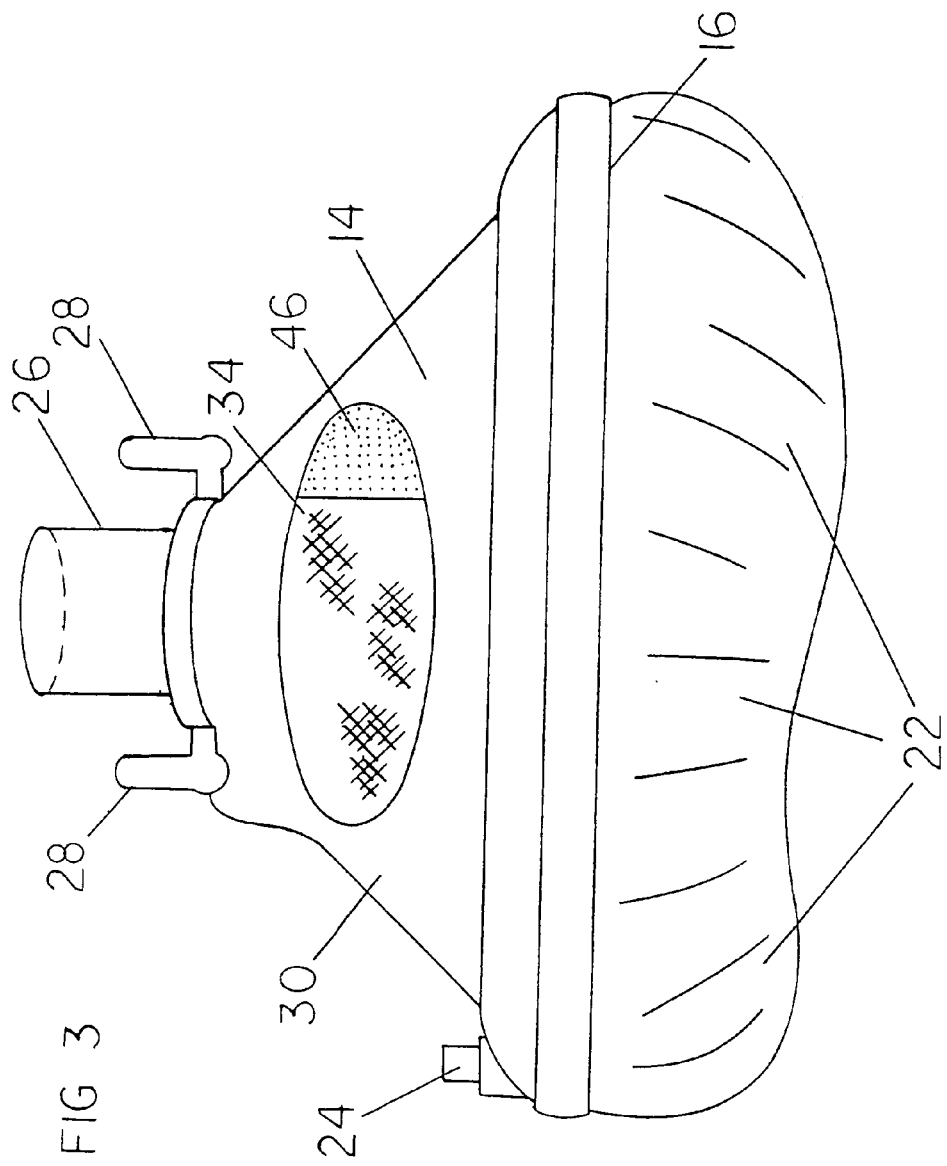
FIG. 3 is a side elevational view of the respiratory anesthesia mask system shown in FIGS. 1 and 2.

With reference now to the drawings, and in particular to FIG. 1 thereof, the preferred embodiment of the new and improved medical system embodying the principles and concepts of the present invention and generally designated by the reference numeral 10 will be described.

The present invention, the medical system 10 is comprised of a plurality of components. Such components in their broadest context include a respiratory anesthesia mask with eyelid closure and protection equipment. Such components are individually configured and correlated with respect to each other so as to attain the desired objective.

First provided is a respiratory anesthesia mask 14. The mask is adapted to receive and removably support eyelid closure and protection equipment. In this manner, patient eye safety is prioritized. The mask has an exposed face. The mask has an interior periphery 16. The interior periphery is provided in a continuous loop. The interior periphery is ergonomically designed to fit the contours of a face of a patient. The interior periphery is designed in a comfortable manner for the patient. The interior periphery is further designed to avoid physical contact with the eyes of the patient. The mask has a caudad portion 18. The caudad portion has a broad width. The mask has a cephalad portion 20. The cephalad portion has a narrow width less than the broad portion. The mask has an air-filled tubular bladder 22. The bladder is provided in a continuous loop. The bladder is provided overlying the interior periphery. In this manner, patient comfort is enhanced through a cushioned mask fit while a low pressure seal is provided between the mask and a face of the user. A valve 24 is coupled to the bladder for increasing and decreasing the pressure within the bladder. A syringe is adapted to function with the bladder for adding air and removing air from the bladder to optimize the fit of the mask on a face of a patient.

The mask has a centrally located exterior cylinder 26. The exterior cylinder is adapted to couple with a source of respiratory anesthesia gas for delivery to a patient. The cylinder has a ring with hooks 28 to facilitate coupling the mask to a patient with a strap or fastening device. The ring and hooks are adapted to be color coded to facilitate identifying size-indicating colors.

The mask has an intermediate section 30. The intermediate section is in a generally frusto-conical configuration. The intermediate section is provided between the interior periphery and the tube. The mask is fabricated of a hypo-allergenic plastic. In this manner, the comfort and safety of the patient are enhanced. The mask is adapted to be fabricated of non-latex, sterile or non-sterile materials. The plastic of the mask is clear and transparent, preferably a thermoset hard plastic. In this manner, uninterrupted surveillance of the patient and readily exhibited condensation characteristic of expiration of gas from the patient are provided. The mask is intended for single patient use. In this manner, costly sterilization and reprocessing expenses are eliminated. Also in this manner, contamination of medical equipment from one patient to another is prevented.

Eyelid closure and protection equipment 34 is provided. The closure and protection equipment is received and supported on the face of the intermediate section of the mask on opposite sides of the cylinder. The closure and protection equipment includes two oval-shaped fixed release strips 36. The fixed release strips have interior and exterior surfaces. A permanent adhesive 38 is provided. The permanent adhesive is provided on the entire interior surface of the fixed release strip. In this manner, the fixed release strips are permanently coupled to the face of the intermediate section of the mask. The closure and protection equipment includes two oval shaped two repositionable adhesive strips 40. The repositionable adhesive strips have interior and exterior surfaces. A temporary adhesive 42 is provided. The temporary adhesive is provided on between 60 and 90 percent of interior surface of the repositionable adhesive strips. In this manner, the repositionable adhesive strips are adjustably coupled to the exterior surfaces of the fixed release strips. The fixed release strips and the repositionable adhesive strips are each provided in an oval configuration. The fixed release strips and the repositionable adhesive strips each have a major axis between 1.5 and 2.5 inches and a minor axis between 1 and 1.5 inches. The portions of the repositionable adhesive strips without adhesive 46 are provided closer to the caudad portion of the mask than to the cephalad portion of the mask.

The eyelid closure and protection equipment is integrated into the respiratory anesthesia mask, one at each side with repositionable adhesive strips. The dimensions of the repositionable adhesive strips exceed the size of a human eye. In this manner, complete coverage is allowed. The adhesive properties are only adapted to apply to the side of the repositionable adhesive strips in contact with the fixed release strips. Once removed, during use, the repositionable adhesive strips remain in contact with the patient. The repositionable adhesive strips are intended for single patient use. In this manner, costly sterilization and reprocessing expenses are eliminated. Also in this manner, contamination of medical equipment from one patient to another is prevented. The repositionable adhesive strips are non-latex. In this manner, the risk of latex exposure, latex allergy, and latex sensitization for patient and healthcare provider is prevented. The repositionable adhesive strips have hypoallergenic properties. In this manner, irritation of the eyes, eyelids, and surrounding skin is reduced. The strips are waterproof. In this manner, the equipment is protected from loss of integrity and adhesion and able to maintain eyelid closure and protection. The strips are transparent. In this manner, uninterrupted surveillance of the patient is allowed.

Tabs are provided. The tabs are formed as parts of the repositionable adhesive strips. The tabs are formed without adhesive there beneath. In this manner, the adhesive strips will remain attached to the mask until the healthcare provider efficiently lifts the tabs and raises the entire repositionable adhesive strip efficiently just prior to application to the patient. The tab is a raised edge of one of the repositionable adhesive strips with no adhesive but contiguous with the remainder of the repositionable adhesive strip which has adhesive on its undersurface. The tab is adapted to be grasped and pulled by the health care provider. In this manner, careful removal of the strip from the patient at the conclusion of use, whether for both procedure and general anesthetic, is facilitated. Further in this manner, trauma to and bruising of the eyelid is prevented. The repositionable adhesive strips are located on the mask. The repositionable strips are always visible to the healthcare provider as he monitors the patient. The presence and position of the repositionable strips thereby serve as a constant reminder to employ the eye protection measure as soon as loss of consciousness is achieved and lessen the chance of distractions and interruptions, normally common during clinical activities of this busy period, which can impact timely performance and increase the risk of errors of omission and patient injury.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desires to be protected by LETTERS PATENT of the United States is as follows:

1. A medical system comprising:
    a respiratory anesthesia mask having an exposed face, the mask having an interior periphery in a continuous loop to fit a face of a patient, the mask having a centrally located exterior cylinder adapted to couple with a source of respiratory anesthesia gas, the mask having an intermediate section in a generally frusto-conical configuration between the interior periphery and the exterior cylinder, the mask having a caudad portion with a broad width, the mask having a cephalad portion with a narrow width less than the broad width of the caudad portion, the caudad and cephalad portions are with respect to patient orientation; and
    an eyelid closure and protection equipment received and supported on the intermediate section of the mask, the eyelid closure and protection equipment including two repositionable adhesive strips with interior and exterior surfaces, each repositionable adhesive strip adapted to adhere to an eyelid of the patient and having a coupling portion and a second portion, a temporary adhesive on the interior surface of each of the coupling portions of the repositionable adhesive strips for releasably coupling the repositionable adhesive strips to the intermediate section of the mask, the second portions of the repositionable adhesive strips being closer to the caudad portion of the mask than to the cephalad portion of the mask; and
    the eyelid closure and protection equipment further including two fixed release strips in any myriad shapes with interior and exterior surfaces, a permanent adhesive on the entire interior surfaces of the fixed release strips permanently coupling the fixed release strips to the intermediate section of the mask, and wherein the temporary adhesive on at least a portion of the interior surface of the repositionable adhesive strips releasably couples the repositionable adhesive strips to the exterior surfaces of the fixed release strips.

2. The system as set forth in claim 1 wherein the fixed release strips and the repositionable adhesive strips are each in any myriad of shapes in a longitudinal configuration with a major axis between approximately 1.5 and 2.5 inches and a minor axis between approximately 1 and 1.5 inches.

3. The system as set forth in claim 1 wherein the fixed release strips and the repositionable adhesive strips are each created of varying sizes appropriate for children and adults.

4. The system as set forth in claim 1 wherein the fixed release strips are fabricated of a flexible material.

5. The system as set forth in claim 4 wherein the fixed release strips are hypo-allergenic.

6. The system as set forth in claim 4 wherein the fixed release strips are clear.

7. The system as set forth in claim 4 wherein the fixed release strips are fabricated of a plastic material.

8. The system as set forth in claim 1 wherein the repositionable adhesive strips are fabricated of a flexible material.

9. The system as set forth in claim 8 wherein the repositionable adhesive strips are hypo-allergenic.

10. The system as set forth in claim 8 wherein the repositionable adhesive strips are clear.

11. The system as set forth in claim 8 wherein the repositionable adhesive strips are fabricated of a plastic material.

* * * * *

UNITED STATES PATENT AND TRADEMARK OFFICE
CERTIFICATE OF CORRECTION

PATENT NO. : 8,413,656 B2  
APPLICATION NO. : 13/066069  
DATED : April 9, 2013  
INVENTOR(S) : Julio A. Warren Page 1 of 1

It is certified that error appears in the above-identified patent and that said Letters Patent is hereby corrected as shown below:

Title Page, Item (76) Inventor should read

(76) Inventor: Julio A. Warren, St. Petersburg, FL (US)

Signed and Sealed this  
Second Day of July, 2013

Teresa Stanek Rea  
*Acting Director of the United States Patent and Trademark Office*